United States Patent
Tran et al.

(10) Patent No.: US 6,906,206 B2
(45) Date of Patent: Jun. 14, 2005

(54) ANTIDEPRESSANT AZAHETEROCYCLYLMETHYL DERIVATIVES OF 1,4,5-TRIOXA-PHENANTHRENE

(75) Inventors: Megan Tran, Hoboken, NJ (US); Gary P. Stack, Ambler, PA (US)

(73) Assignee: Wyeth, Madison, NJ (US)

( * ) Notice: Subject to any disclaimer, the term of this patent is extended or adjusted under 35 U.S.C. 154(b) by 103 days.

(21) Appl. No.: 10/377,850

(22) Filed: Mar. 3, 2003

(65) Prior Publication Data

US 2003/0225157 A1 Dec. 4, 2003

Related U.S. Application Data

(63) Continuation-in-part of application No. 10/132,238, filed on Apr. 25, 2002, now Pat. No. 6,555,560.
(60) Provisional application No. 60/287,448, filed on Apr. 30, 2001.

(51) Int. Cl.⁷ .............................................. C07D 493/04
(52) U.S. Cl. ......................................................... 549/361
(58) Field of Search ........................................ 549/361

(56) References Cited

U.S. PATENT DOCUMENTS

| | | |
|---|---|---|
| 5,318,988 A | 6/1994 | Schohe-Loop et al. |
| 5,371,094 A | 12/1994 | Heine et al. |
| 5,741,789 A | 4/1998 | Hibschman et al. |
| 5,824,682 A | 10/1998 | Van Lommen et al. |
| 5,869,490 A | 2/1999 | Stack et al. |

FOREIGN PATENT DOCUMENTS

| | | |
|---|---|---|
| EP | 0 771 800 A2 | 5/1997 |
| EP | 0 963 983 A1 | 5/1999 |
| WO | WO 91/13872 | 9/1991 |

*Primary Examiner*—Patricia L. Morris
(74) *Attorney, Agent, or Firm*—Woodcock Washburn LLP

(57) ABSTRACT

Compounds of the formula

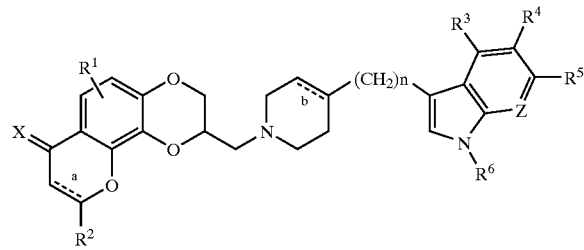

useful for the treatment of diseases such as depression (including but not limited to major depressive disorder, childhood depression and dysthymia), anxiety, panic disorder, post-traumatic stress disorder, premenstrual dysphoric disorder attention deficit disorder (with and without hyperactivity), obsessive compulsive disorder (including trichotillomania), social anxiety disorder, generalized anxiety disorder, obesity, eating disorders such as anorexia nervosa, bulimia nervosa, vasomotor flushing, cocaine and alcohol addiction, sexual dysfunction and related illnesses.

2 Claims, No Drawings

ANTIDEPRESSANT AZAHETEROCYCLYLMETHYL DERIVATIVES OF 1,4,5-TRIOXA-PHENANTHRENE

This application is a divisional of application Ser. No. 10/132,238, filed on Apr. 25, 2002, now U.S. Pat. No. 6,555,560, which claims benefit of provisional application Ser. No. 60/287,448, filed Apr. 30, 2001, the entire disclosure of which is hereby incorporated by reference.

BACKGROUND OF THE INVENTION

Major depression is a serious health problem affecting more than 5% of the population, with a life-time prevalence of 15–20%.

Selective serotonin reuptake inhibitors have produced significant success in treating depression and related illnesses and have become among the most prescribed drugs. They nonetheless have a slow onset of action, often taking several weeks to produce their full therapeutic effect. Furthermore, they are effective in fewer than two-thirds of patients.

Serotonin selective reuptake inhibitors (SSRIs) are well known for the treatment of depression and other conditions. SSRIs work by blocking the neuronal reuptake of serotonin, thereby increasing the concentration of serotonin in the synaptic space, and thus increasing the activation of postsynaptic serotonin receptors.

However, although a single dose of an SSRI can inhibit the neuronal serotonin transporter which would be expected to increase synaptic serotonin, long-term treatment is required before clinical improvement is achieved.

It has been suggested that the SSRIs increase the serotonin levels in the vicinity of the serotonergic cell bodies and that the excess serotonin activates somatodendritic autoreceptors, 5-HT$_{1A}$ receptors, causing a decrease in serotonin release in major forebrain areas. This negative feedback limits the increment of synaptic serotonin that can be induced by antidepressants.

A 5-HT$_{1A}$ antagonist wouldt limit the negative feedback and should improve the efficacy of the serotonin reuptake mechanism. (Perez, V., et al., *The Lancet,* 349:1594–1597 (1997)). Such a combination therapy would be expected to speed up the effect of the serotonin reuptake inhibitor.

Thus, it is highly desirable to provide improved compounds which both inhibit serotonin reuptake and which are antagonists of the 5-HT$_{1A}$ receptor.

DESCRIPTION OF THE INVENTION

In accordance with this invention, there is provided a group of novel compounds of the formula:

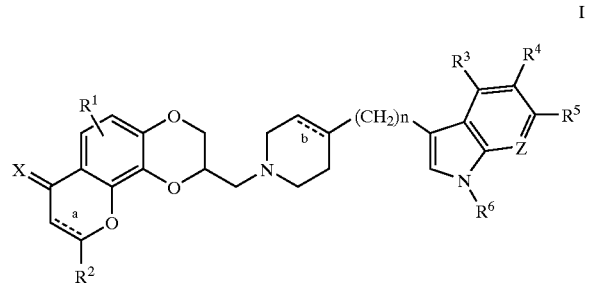

I wherein $R^1$, $R^3$, $R^4$, $R^5$ and $R^7$ are, independently, hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$ and $R^6$ are hydrogen or alkyl of 1 to 6 carbon atoms;

Z is $CR^7$ or N;

X is O, S, $H_2$ or $F_2$;

the dotted lines at a and b represent independently optional double bonds; and n is an integer 0, 1 or 2;

or a pharmaceutically acceptable salt thereof.

In some preferred embodiments of the present invention, $R^1$ is hydrogen, hydroxy, halo, cyano, trifluoromethyl, alkyl of one to six carbon atoms or alkoxy of one to six carbon atoms. In still more preferred embodiments of the present invention, $R^1$ is hydrogen, halo and methoxy.

In other embodiments of the invention $R^2$ is preferably hydrogen or lower alkyl. $R^2$ is still more preferably hydrogen.

$R^3$, $R^4$, and $R^5$ are preferably independently selected from hydrogen, hydroxy, halo, cyano, carboxamido, alkyl of one to six carbon atoms, and alkoxy of one to six carbon atoms in some embodiments of the invention. Still more preferably $R^3$, $R^4$, and $R^5$ are preferably independently selected from hydrogen, cyano and halogen.

$R^6$ is preferably hydrogen or lower alkyl.

X is preferably O or $H_2$.

Of the compounds of Formula I, still more preferred are those in which $R^1$ is hydrogen, hydroxy, halo, cyano, trifluoromethyl, alkyl of one to six carbon atoms or alkoxy of one to six carbon atoms; $R^2$ is hydrogen, methyl or ethyl; $R^3$, $R^4$, and $R^5$ are preferably independently selected from hydrogen, hydroxy, halo, cyano, carboxamido, alkyl of one to six carbon atoms, and alkoxy of one to six carbon atoms, Z is $CR^7$, $R^7$ is hydrogen, hydroxy, halo, cyano, carboxamido, alkyl of one to six carbon atoms, or alkoxy of one to six carbon atoms; n is an integer 0 or 1; and $R^6$ and the dotted lines are defined as above.

Most preferred are those examples in which $R^1$ is hydrogen, halo or methoxy, $R^2$ and $R^6$ are hydrogen, $R^3$, $R^4$, and $R^5$ are preferably independently selected from hydrogen, halo and cyano, Z is $CR^7$, $R^7$ is hydrogen, halo or cyano, n is 0 and the dotted line in the azaheterocycle represents a double bond.

This invention relates to both the R and S stereoisomers of the aminomethyl-1,4,5-trioxa-phenanthrene, as well as to mixtures of the R and S stereoisomers. Throughout this application, the name of the product of this invention, where the absolute configuration of the aminomethyl-1,4,5-trioxa-phenanthrene is not indicated, is intended to embrace the individual R and S enantiomers as well as mixtures of the two. In some preferred embodiments of the present invention the S stereoisomer is preferred.

Where a stereoisomer is preferred, it may, in some embodiments be provided substantially free of the corresponding enantiomer. Thus, an enantiomer substantially free of the corresponding enantiomer refers to a compound which is isolated or separated via separation techniques or prepared free of the corresponding enantiomer. Substantially free as used herein means that the compound is made up of a significantly greater proportion of one stereoisomer. In preferred embodiments the compound is made up of at least about 90% by weight of a preferred stereoisomer. In other embodiments of the invention, the compound is made up of at least about 99% by weight of a preferred stereoisomer. Preferred stereoisomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, N.Y., 1981); Wilen, S. H., et al., *Tetrahedron* 33:2725 (1977); Eliel, E. L. *Stereochemistry of Carbon Compounds* (McGraw-Hill, N.Y., 1962); Wilen, S. H. *Tables of Resolving Agents and Optical Resolutions* p. 268 (E. L. Eliel, Ed., Univ. of Notre Dame Press, Notre Dame, Ind. 1972).

Alkyl as used herein refers to an aliphatic hydrocarbon chain and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 3 carbon atoms.

Alkanamido as used herein refers to the group R—C(=O)—NH— where R is an alkyl group of 1 to 5 carbon atoms.

Alkanoyloxy as used herein refers to the group R—C(=O)—O— where R is an alkyl group of 1 to 5 carbon atoms.

Alkanesulfonamido as used herein refers to the group R—S(O)$_2$—NH— where R is an alkyl group of 1 to 6 carbon atoms.

Alkoxy as used herein refers to the group R—O— where R is an alkyl group of 1 to 6 carbon atoms.

Carboxamido as used herein refers to the group —CO—NH$_2$.

Carboalkoxy as used herein refers to the group R—O—C(=O)— where R is an alkyl group of 1 to 5 carbon atoms.

Halogen (or halo) as used herein refers to chlorine, bromine, fluorine and iodine.

Pharmaceutically acceptable salts are those derived from such organic and inorganic acids as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific compounds of the present invention are:

3-[4-(5-fluoro-1H-indol-3-yl)-3,6-dihydro-2H-pyridin-1-ylmethyl]-2,3-dihydro-7H-pyrano[2,3-f][1,4]benzodioxin-7-one;

5-fluoro-3-[1,2,3,6-tetrahydro-1-[(2,3,8,9-tetrahydro-7H-pyrano[2,3-f][1,4]-benzodioxin-2-yl)methyl]-4-pyridinyl]-1H-indole;

3-[4-(1H-indol-3-yl)-3,6-dihydro-2H-pyridin-1-ylmethyl]-2,3,6,7-tetrahydro-1,4,5-trioxa-phenanthren-8-one; and 3-{1-(2,3,8,9-tetrahydro-7H-[1,4]dioxino[2,3-h]chromen-2-ylmethyl)-1,2,3,6-tetrahydropyridin-4-yl}-1H-indole; and pharmaceutical salts thereof.

Further in accordance with the present invention is provided novel intermediates of the formula:

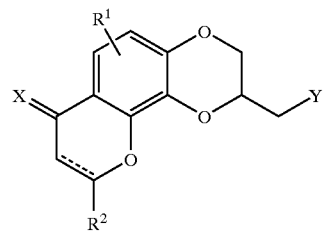

II wherein
  $R^1$ is hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;
  $R^2$ is hydrogen or alkyl of 1 to 6 carbon atoms;
  X is O, S, H$_2$ or F$_2$; and
  Y is hydroxy, halogen, alkylsulfonate of 1 to 6 carbon atoms, trifluoromethanesulfonate or benzenesulfonate, in which the benzene ring is optionally substituted with halogen, nitro, trifluoromethyl, cyano, alkyl of 1 to 6 carbon atoms or alkoxy of 1 to 6 carbon atoms, and the dotted lines at a and b represent, independently, optional double bonds,
which are useful for the production of agents for the treatment of depression and other central nervous system disorders.

Specific compounds of Formula II are:
  [7-Oxo-2,3-dihydro-7H-[1,4]dioxino[2,3-h]chromen-2-yl]methyl 4-methylbenzenesulfonate;
  2,3,8,9-Tetrahydro-7H[1,4]dioxino[2,3-h]chromen-2-ylmethyl 4-methylbenzenesulfonate; and
  [7-Oxo-2,3,8,9-tetrahydro-7H-[1,4]dioxino[2,3-h]chromen-2-yl]methyl 4-methylbenzenesulfonate.

The 2-azaheterocyclylmethyl-1,4,5-trioxa-phenanthrenes in which $R^1$ is H are prepared as illustrated below. Unless otherwise noted, the variables are as defined above. Specifically, 2',3',4'-trihydroxyacetophenone (1) is regioselectively alkylated with glycidyl tosylate or halide in the presence of a suitable base such as sodium carbonate to give the benzodioxan moiety (2). Condensation with the appropriate N,N-dimethylalkanamide dimethylacetal, followed by Scheme I

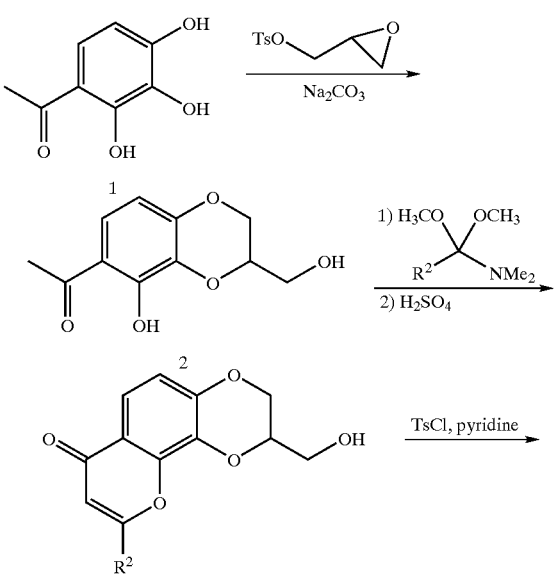

-continued

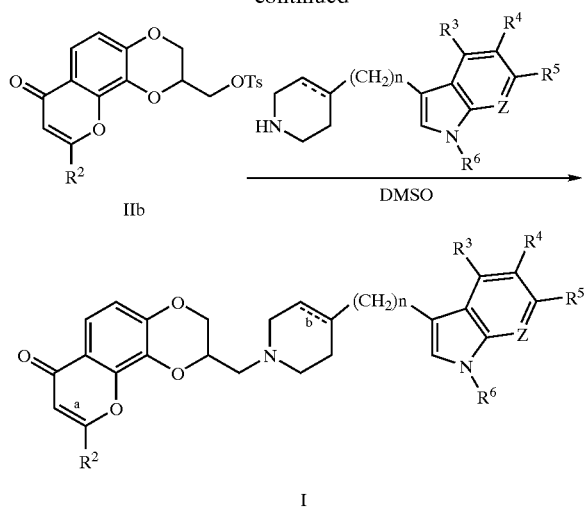

cyclization with sulfuric acid gives the chromone (IIa). Conversion to the tosylate (IIb) via treatment with p-toluenesulfonyl chloride in pyridine or to a halide by reaction with carbon tetrabromide or carbon tetrachloride in combination with triphenylphosphine and replacement of the tosylate or halide with the azaheterocycles appropriate to the invention yields the title compounds.

The chromone (IIb) described above is alternatively reduced to the chromane (IId) via treatment with hydrogen over platinum oxide or to the chromanone via transfer hydrogenation using ammonium formate and palladium on carbon in methanol as shown in Scheme II below. Again, the title compounds of the invention are derived by replacement of the tosylate or halide with the amines appropriate to the invention in a high boiling solvent such as DMSO.

The chromones appropriate for the invention may be alternatively prepared as shown in Scheme III below. The appropriate mono-allylated catechol (5) is elaborated with glycidyl tosylate as described above to produce (6) and rearranged in refluxing mesitylene. Cyclization to the benzodioxan methanol (7) is effected by treatment with sodium bicarbonate in ethanol and the alcohol is converted to the tosylate or halide as described above. After rearrangement of the double bond by treatment with catalytic bis-acetonitrile palladium (II) chloride in refluxing methylene chloride to produce (8) and cleavage with ozone or osmium tetroxide/sodium periodate as described above, the resulting aldehyde (9) is converted to the phenol (10) via oxidation with a suitable oxidant such as meta-chloroperoxybenzoic acid (a Baeyer-Villager reaction) followed by cleavage of the resulting formate with methanol and basic alumina. A condensation with the appropriately substituted acylacetate in the Scheme III

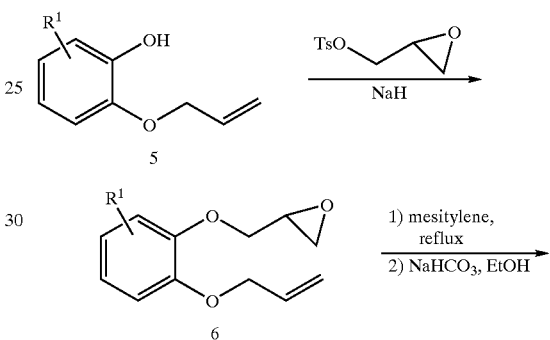

Scheme II

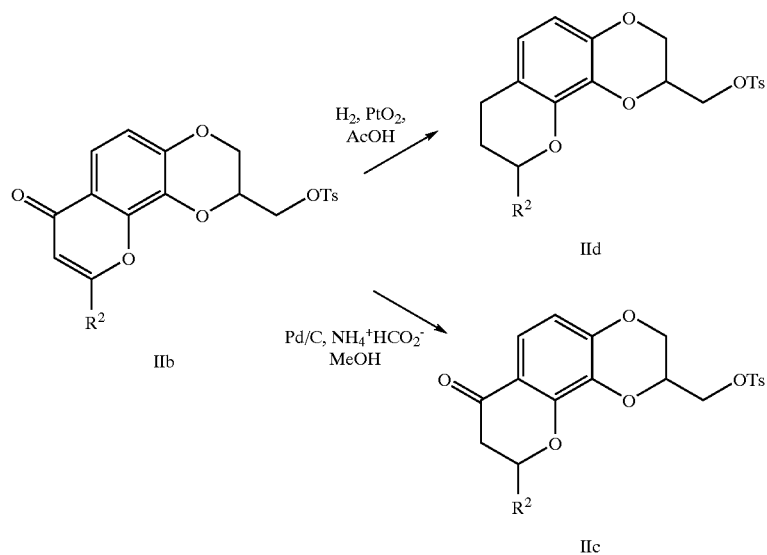

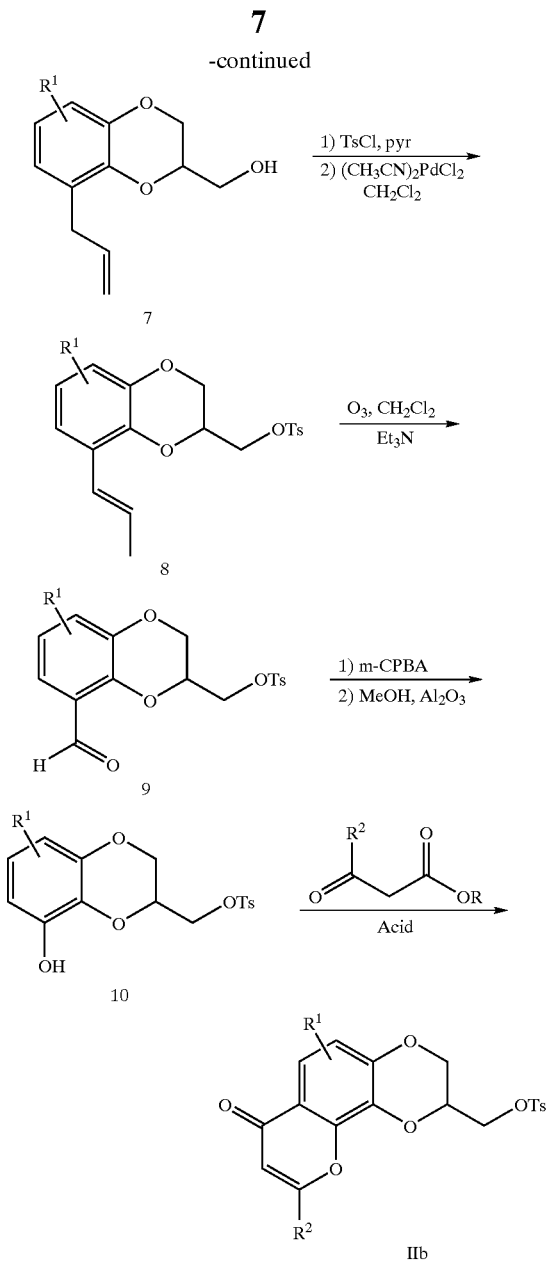

presence of an acid such as polyphosphoric acid, sulfuric acid or phosphorus pentoxide gives the substituted chromone (IIb) appropriate for the compounds of the invention.

The acetophenones, catechols and azaheterocycles appropriate to the above chemistry are known compounds or can be prepared by one schooled in the art. The compounds of the invention may be resolved into their enantiomers by conventional methods or, preferably, the individual enantiomers may be prepared directly by substitution of (2R)-(−)-glycidyl 3-nitrobenzenesulfonate or tosylate (for the S benzodioxan methanamine) or (2S)-(+)-glycidyl 3-nitrobenzenesulfonate or tosylate (for the R enantiomer) in place of epihalohydrin or racemic glycidyl tosylate in the procedures above.

A protocol similar to that used by Cheetham et. al. (Neuropharmacol. 32:737, 1993) was used to determine the affinity of the compounds of the invention for the serotonin transporter. The compound's ability to displace $^3$H-paroxetine from male rat frontal cortical membranes was determined using a Tom Tech filtration device to separate bound from free $^3$H-paroxetine and a Wallac 1205 Beta Plate® counter to quantitate bound radioactivity. $K_i$'s thus determined for standard clinical antidepressants are 1.96 nM for fluoxetine, 14.2 nM for imipramine and 67.6 nM for zimelidine. A strong correlation has been found between $^3$H-paroxetine binding in rat frontal cortex and $^3$H-serotonin uptake inhibition.

High affinity for the serotonin 5-HT$_1$A receptor was established by testing the claimed compound's ability to displace [$^3$H] 8-OHDPAT (dipropylaminotetralin) from the 5-HT$_1$A serotonin receptor following a modification of the procedure of Hall et al., J. Neurochem. 44, 1685 (1985) which utilizes CHO cells stably transfected with human 5-HT$_1$A receptors. The 5-HT$_1$A affinities for the compounds of the invention are reported below as $K_i$'s.

Antagonist activity at 5-HT$_1$A receptors was established by using a $^{35}$S-GTPγS binding assay similar to that used by Lazareno and Birdsall (Br. J. Pharmacol. 109: 1120, 1993), in which the test compound's ability to affect the binding of $^{35}$S-GTPγS to membranes containing cloned human 5-HT$_1$A receptors was determined. Agonists produce an increase in binding whereas antagonists produce no increase but rather reverse the effects of the standard agonist 8-OHDPAT. The test compound's maximum inhibitory effect is represented as the $I_{max}$, while its potency is defined by the IC$_{50}$.

The results of the three standard experimental test procedures described in the preceding three paragraphs were as follows:

| Compound | 5-HT Transporter Affinity KI (nM) | 5-HT$_{1A}$ Receptor Affinity KI (nM) | 5-HT$_{1A}$ Function IC$_{50}$ (nM) (I$_{max}$) |
|---|---|---|---|
| Example 1 | 2.69 | 118.90 | 2.37 (100) |
| Example 2 | 2.57 | 27.61 | 0.56 (100) |
| Example 3 | 2.74 | 155.90 | |
| Example 4 | 0.90 | 44.12 | 0.38 (87.0) |

Like the antidepressants fluoxetine, paroxetine and sertraline, the compounds of this invention have the ability to potently block the reuptake of the brain neurotransmitter serotonin. They are thus useful for the treatment of diseases commonly treated by the administration of serotonin selective reuptake inhibitor (SSRI) antidepressants, such as depression (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive compulsive disorder (including trichotillomania), social anxiety disorder, generalized anxiety disorder, obesity, eating disorders such as anorexia nervosa, bulimia nervosa, vasomotor flushing, cocaine and alcohol addiction, sexual dysfunction (including premature ejaculation), and related illnesses. Moreover, the compounds of this invention have potent affinity for and antagonist activity at brain 5-HT$_1$A serotonin receptors. Recent clinical trials employing drug mixtures (eg, fluoxetine and pindolol) have demonstrated a more rapid onset of antidepressant efficacy for a treatment combining SSRI activity and 5-HT$_1$A antagonism (Blier and Bergeron, 1995; F. Artigas et. al., 1996; M. B. Tome et. al., 1997). The compounds of the invention are exceedingly interesting and useful for treating depressive illnesses.

Thus the present invention provides methods of treating, preventing, inhibiting or alleviating each of the maladies listed above in a mammal, preferably in a human, the methods comprising providing a pharmaceutically effective amount of a compound of this invention to the mammal in need thereof.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in *Remingtons Pharmaceutical Sciences*, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 5 mg per day with gradual increase in the daily dose to about 150 mg per day, to provide the desired dosage level in the human.

Provide as used herein means either directly administering a compound or composition of the present invention, or administering a prodrug, derivative or analog which will form an equivalent amount of the active compound or substance within the body.

The present invention includes prodrugs of compounds of Formula I. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991), Bundgaard, et al., Journal of Drug Deliver Reviews, 8:1–38(1992), Bundgaard, J. of Pharmaceutical Sciences, 77:285 et seq. (1988); and Higuchi and Stella (eds.) Prodrugs as Novel Drug Delivery Systems, American Chemical Society (1975).

The following examples illustrate the production of representative compounds of this invention.

Intermediate 1

1-[5-Hydroxy-3-(hydroxymethyl)-2,3-dihydro-1,4-benzodioxin-6-yl]-1-ethanone

To a solution of 2',3',4'-trihydroxyacetophenone (10.6 g, 63.0 mmole) in DMF (75 mL) was added potassium carbonate (17.4 g, 126 mmole). After 5 minutes (R)-glycidyl tosylate (9.67 g, 42.3 mmole) was added then the heterogeneous mixture was heated to 70° C. for 3 hours. After removal of the solvent in vacuum, the residue was taken into water (800 mL) and was then extracted with ethyl acetate (4×300 mL). The combined organic layers were dried over $MgSO_4$, filtered and evaporate to dryness in vacuum. The crude brown oil thus obtained was column chromatographed on silica gel with 40% hexane/ethyl acetate as eluant to give the (S)-enantiomer of the title compound as a yellow oil which solidifies upon standing (7.5 g, 78%). MS (ESI) m/z 223 (M−H)−.

Elemental Analysis for: $C_{11}H_{12}O_5 \cdot 0.10H_2O$ Calc'd: C, 58.46; H, 5.44 Found: C, 58.02; H, 5.09

Intermediate 2

2-(Hydroxymethyl)-2,3-dihydro-7H-[1,4]dioxino[2,3-h]chromen-7-one

To a solution of 1-[(3S)-5-hydroxy-3-(hydroxymethyl)-2,3-dihydro-1,4-benzodioxin-6-yl]-1-ethanone (0.75 g, 3.35 mmole) in xylenes (50 mL) was added N,N-dimethylformamide dimethyl acetal (0.65 mL, 4.89 mmole). The solution was heated to 120° C. for 45 minutes under nitrogen. Upon cooling to room temperature, a yellow solid β-amino enone intermediate precipitated from solution and was filtered. Cyclization of this intermediate was effected by treatment with a mixture of 5 mL of concentrated sulfuric acid and 25 mL of water for 1 hour at room temperature. The mixture was then diluted to 200 mL with water and extracted with 200 mL of ethyl acetate. The extract was dried over magnesium sulfate. After filtration and evaporation in vacuum, the crude product was column chromatographed on silica gel with 2% methanol/methylene chloride to give 0.66 g (85%) of the product, the (S)-enantiomer of the title compound, as a white solid, m.p. 125° C. MS (+APCI) m/z 235 (M+H)+.

Elemental Analysis for: $C_{12}H_{10}O_5.0.25H_2O$ Calc'd: C, 60.38; H, 4.43 Found: C, 60.13; H, 4.83

Intermediate 3

[7-Oxo-2,3-dihydro-7H-[1,4]dioxino[2,3-h]chromen-2-yl]methyl 4-methylbenzenesulfonate p-Toluenesulfonyl chloride (0.60 g, 3.15 mmole) was added to solution of (2S)-2-(hydroxymethyl)-2,3-dihydro-7H-[1,4]dioxino[2,3-h]chromen-7-one (0.41 g, 1.75 mmole) in 50 mL of pyridine. The solution was stirred at room temperature overnight under nitrogen. Water was added to quench the excess tosyl chloride and the solvent was removed in vacuum and replaced with methylene chloride. The solution was washed with 2N aqueous HCl, with saturated aqueous sodium bicarbonate, and with saturated brine, and dried over magnesium sulfate. Filtration, evaporation in vacuum and column chromatography on silica gel with 3% methanol/methylene chloride as eluant gave 0.36 g (54%) of the (R)-enantiomer of the title compound as a yellow solid, m.p. 190–191° C.

Elemental Analysis for: $C_{19}H_{16}O_7S.0.20H_2O$ Calc'd: C, 58.22; H, 4.22 Found: C, 57.88; H, 3.93

EXAMPLE 1

3-[4-(5-Fluoro-1H-indol-3-yl)-3,6-dihydro-2H-pyridin-1-ylmethyl]-2,3-dihydro-7H-pyrano[2,3-f][1,4]benzodioxin-7-one

[(2R)-7-Oxo-2,3-dihydro-7H-[1,4]dioxino[2,3-h]chromen-2-yl]methyl 4-methylbenzenesulfonate (0.50 g, 1.28 mmole) and 5-fluoro-3-(4-piperidinylmethyl)-1H-indole (0.27 g, 1.26 mmole) were combined in 25 mL of DMSO under nitrogen. This solution was heated to 75-80° C. for 4 hours under nitrogen. After completion, the reaction was cooled to room temperature and partitioned between ethyl acetate and saturated aqueous sodium bicarbonate. The organic phase was washed with brine, dried over magnesium sulfate and concentrated in vacuum. The crude residue was column chromatographed on silica gel using methylene chloride to remove impurities. A solution of 3% methanol/methylene chloride eluted the product, which was obtained as a yellow oil. The oil was crystallized from ethanol with the addition of a solution of fumaric acid in hot ethanol to give 0.040 g of the (S)-enantiomer of the title compound as a yellow solid fumarate dihydrate, m.p. 106–108° C.

Elemental Analysis for: $C_{25}H_{21}FN_2O_4.C_4H_4O_4.2H_2O$ Calc'd: C, 59.59; H, 5.00; N, 4.79 Found: C,59.32; H, 4.72; N, 4.64

Intermediate 4

(2R)-2,3,8,9-Tetrahydro-7H[1.41]dioxino[2,3-h]chromen-2-ylmethyl 4-methylbenzenesulfonate

[(2R)-7-Oxo-2,3-dihydro-7H-[1,4]dioxino[2,3-h]chromen-2-yl]methyl 4-methylbenzenesulfonate (1.0 g, 2.6 mmole) dissolved in acetic acid (50 mL) was hydrogenated at 40 psi in the presence of 0.30 g platinum oxide on a Parr shaker for 5 hours. The catalyst was filtered through celite and the filter cake washed with water. The filtrate was then extracted with ethyl acetate and the organic layer was washed with saturated sodium bicarbonate until neutral. The organic extracts were dried over magnesium sulfate, filtered and evaporated to give 0.78 g (81%) of the (R)-enantiomer of the title compound as a clear oil. $^1$H (CDCl$_3$) doublet 7.8 δ (2H); doublet 7.4 δ (2H); singlet 6.5 δ (1H); singlet 6.4 δ (1H); multiplet 4.2 δ (1H); multiplet 4.1–4.3 δ (5H); multiplet 4.0 δ (1H); triplet 2.7 δ (2H); singlet 2.4 δ (3H); triplet 2.0 δ (2H).

EXAMPLE 2

5-Fluoro-3-[1,2,3,6-tetrahydro-1-[(2,3,8,9-tetrahydro-7H-pyrano[2,3-f][4,1]benzodioxin-2-yl)methyl]-4-pyridinyl]-1H-indole To a mixture of (2R)-2,3,8,9-tetrahydro-7H-[1,4]dioxino[2,3-h]chromen-2-ylmethyl 4-methylbenzenesulfonate (0.25 g, 0.66 mmole) and potassium carbonate (0.22 g, 1.55 mmole) in 1:1 tetrahydrofuran/dimethylformamide (20 mL) was added 0.45 g (2.08 mmole) of 5-fluoro-3-(1,2,3,6-tetrahydro-4-pyridinyl)-1H-indole. The reaction mixture was refluxed under nitrogen for six hours. After completion, the mixture was evaporated to dryness under reduced pressure and the residue was column chromatographed on silica gel with methylene chloride to remove impurities and 4% methanol/methylene chloride to elute the desired product as an oil, which was crystallized from isopropanol with the addition of a solution of oxalic acid in hot isopropanol to give 0.040 g (6%) of the (S)-enantiomer of the title compound as a dark yellow solid, m.p. 146–148° C.

Elemental Analysis for: $C_{25}H_{25}FN_2O_3.C_2H_2O_4.0.75H_2O$ Calc'd: C, 61.89; H, 5.48; N, 5.35 Found: C,61.64; H, 5.38; N, 5.27

Intermediate 5

[7-Oxo-2,3,8,9-tetrahydro-7H-[1.4]dioxino[2.3-h]chromen-2-yl]methyl 4-methylbenzenesulfonate 0.50 g (1.28 mmole) of [(2R)-7-oxo-2,3-dihydro-7H-[1,4]dioxino[2,3-h]chromen-2-yl]methyl 4-methylbenzenesulfonate in methanol was added to a round bottom flask containing 0.40 g of 10% palladium on carbon under a stream of nitrogen, ammonium carbonate was then added and the heterogeneous mixture was heated to reflux for 2.5 hours. After the catalyst was removed by filtration, the filtrate was concentrated in vacuum and the residue column chromatographed on silica gel with 0.5% methanol/methylene chloride as eluant to give 0.30 g (61%) of the (R)-enantiomer of the title compound as a white foam. $^1$H (CDCl$_3$) doublet 7.8 δ (2H); doublet 7.5 δ (1H); doublet 7.4 δ (2H); doublet 6.6 δ (1H); triplet 4.6 δ (2H); multiplet 4–4.5 δ (5H); triplet 2.8 δ (2H); singlet 2.5 δ (3H).

EXAMPLE 3

3-[4-(1H-Indol-3-yl)-3,6-dihydro-2H-pyridin-1-ylmethyl]-2,3,6,7-tetrahydro-1.4,5-trioxa-phenanthren-8-one To a mixture of [(2R)-7-oxo-2,3,8,9-tetrahydro-7H-[1,4]dioxino[2,3-h]-chromen-2-yl]methyl 4-methylbenzenesulfonate (0.60 g, 1.54 mmole) and potassium carbonate (0.22 g, 1.55 mmole) in 1:1 tetrahydrofuran/ dimethyl-formamide (20 mL) was added 0.91 g (4.61 mmole) of 3-(1,2,3,6-tetrahydro-4-pyridinyl)-1H-indole. The reaction mixture was refluxed under nitrogen for 6 hours. After the reaction was complete, the mixture was evaporated to dryness under reduced pressure and the residue was column chromatographed on silica gel with methylene chloride to remove impurities and with 3% methanol/methylene chloride to elute the desired product. Evaporation of the product-containing fractions in vacuum gave 0.12 g (18%) of the (S)-enantiomer of the title compound as an off-white solid, m.p. 210° C.

Elemental Analysis for: $C_{25}H_{24}N_24.0.20H_2O$ Calc'd: C, 71.48; H, 5.85; N, 6.67 Found: C, 71.55; H, 5.74; N, 6.53

EXAMPLE 4

3-{1-(2,3,8,9-Tetrahydro-7H-[1,4]dioxino[2,3-h]chromen-2-ylmethyl)-1,2,3,6-tetrahydropyridin-4-yl}-1H-indole To a mixture of (2R)-2,3,8,9-tetrahydro-7H-[1,4]dioxino[2,3-h]chromen-2-yl-methyl 4-methylbenzenesulfonate (0.30 g, 0.80 mmole) and potassium carbonate (0.22 g, 1.55 mmole) in 1:1 tetrahydrofuran/dimethylformamide (20 mL) was added 0.47 g (2.38 mmole) of 3-(1,2,3,6-tetrahydro-4-pyridinyl)-1H-indole. The reaction mixture was refluxed under nitrogen for 6 hours. After the reaction was complete, the mixture was evaporated to dryness under reduced pressure and the residue was column chromatographed on silica gel with methylene chloride to remove impurities and with 3% methanol/methylene chloride to elute the desired product as an as an oil, which was crystallized from isopropanol with the addition of a solution of oxalic acid in hot isopropanol to give 0.070 g (6%) of the (S)-enantiomer of the title compound as an orange solid, m.p. 140° C.

Elemental Analysis for: $C_{25}H_{26}N_2O_3 \cdot C_2H_2O_4 \cdot H_2O \cdot 0.3 C_3H_8O$ Calc'd: C, 63.40; H, 6.18; N, 5.30 Found: C, 63.32; H, 5.92; N, 5.06

What is claimed is:
1. A compound of the formula

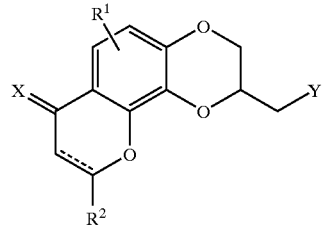

II wherein
$R^1$ is hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;
$R^2$ is hydrogen or ailcyl of 1 to 6 carbon atoms;
X is O, S, $H_2$ or $F_2$, and
Y is hydroxy, halogen, alkylsulfonate of 1 to 6 carbon atoms, trifluoromethanesulfonate or benzenesulfonate, in which the benzene ring is optionally substituted with halogen, nitro, trifluoromethyl, cyano, alkyl of 1 to 6 carbon atoms or alkoxy of 1 to 6 carbon atoms, and
the dotted line represents an optional double bond.
2. A compound of claim 1 which is
[7-Oxo-2,3-dihydro-7H-[1,4]dioxino[2,3-h]chromen-2-yl]methyl4-methylbenzenesulfonate;
2,3,8,9-Tetrahydro-7H[1,4]dioxino[2,3-h]chromen-2-ylmethyl4-methylbenzenesulfonate; or
[7-Oxo-2,3,8,9-tetrahydro-7H-[1,4]dioxino[2,3-h]chromen-2-yl]methyl-4-methylbenzenesulfonate.

* * * * *